(12) United States Patent
Kuiper

(10) Patent No.: US 7,093,773 B2
(45) Date of Patent: Aug. 22, 2006

(54) FRAGRANCE DISPENSER, DOMESTIC APPLIANCE INCLUDING SUCH A FRAGRANCE DISPENSER, AND CARTRIDGE FOR SUCH A FRAGRANCE DISPENSER

(75) Inventor: Bernardus Lubbertus Kuiper, Hoogeveen (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/517,107

(22) PCT Filed: May 21, 2003

(86) PCT No.: PCT/IB03/02200

§ 371 (c)(1),
(2), (4) Date: Dec. 7, 2004

(87) PCT Pub. No.: WO03/105652

PCT Pub. Date: Dec. 24, 2003

(65) Prior Publication Data

US 2005/0224595 A1  Oct. 13, 2005

(30) Foreign Application Priority Data

Jun. 12, 2002  (EP) .................................. 02077293

(51) Int. Cl.
*A61L 9/04* (2006.01)
(52) U.S. Cl. ........................ 239/57; 239/34; 239/58; 239/289; 15/246.3; 422/123
(58) Field of Classification Search .................. 239/34, 239/36, 49, 51.5, 55, 57, 58, 59, 289; 15/246.3; 96/222; 422/122, 123
See application file for complete search history.

(56) References Cited

U.S. PATENT DOCUMENTS

| | | | | |
|---|---|---|---|---|
| 4,554,698 A * | 11/1985 | Rennecker et al. | ............ | 15/339 |
| 5,152,397 A * | 10/1992 | Mayled | ...................... | 206/486 |
| 5,314,669 A * | 5/1994 | Hamilton | ..................... | 422/305 |
| 5,511,278 A | 4/1996 | Shorthill | ..................... | 15/246.2 |
| 5,873,529 A * | 2/1999 | Johnson | ...................... | 239/274 |
| 6,481,639 B1 * | 11/2002 | Pozzo | ......................... | 239/47 |

* cited by examiner

*Primary Examiner*—David A. Scherbel
*Assistant Examiner*—Jason Boeckmann
(74) *Attorney, Agent, or Firm*—Adam L. Stroud

(57) ABSTRACT

An improved fragrance dispenser, domestic appliance, such as a vacuum cleaner, including such a fragrance dispenser, and cartridge for such a fragrance dispenser is provided in which the dispenser includes a housing portion through which an air discharge passage interconnecting an upstream side of the housing portion and a downstream side of the housing portion extends, and a cartridge carrying a fragrant substance and having vents for allowing air to pass for entraining fragrance from said cartridge, wherein the cartridge is removably mounted and rotatably adjustable about an axis of rotation between at least a first position and a second position, at least a portion of at least one of the vents being obstructed by a housing portion if the cartridge is in the first position and being open if the cartridge is in the second position. The cartridge is removable in a direction transverse to the axis of rotation, and the dispenser includes means adapted for engaging and releasing the housing portion in a direction transverse to the axis of rotation. The cartridge contains a granular fragrance carrier substrate.

16 Claims, 2 Drawing Sheets

FRAGRANCE DISPENSER, DOMESTIC APPLIANCE INCLUDING SUCH A FRAGRANCE DISPENSER, AND CARTRIDGE FOR SUCH A FRAGRANCE DISPENSER

BACKGROUND OF THE INVENTION

The invention relates to a fragrance dispenser comprising a housing portion through which an air discharge passage interconnecting an upstream side of said housing portion and a downstream side of said housing portion extends, and a cartridge carrying a fragrant substance and having vents for allowing air to pass for entraining fragrance from said cartridge, wherein the cartridge is removably mounted and rotatably adjustable about an axis of rotation between at least a first position and a second position, at least a portion of at least one of said vents being obstructed by said housing portion if said cartridge is in said first position and being open if said cartridge is in said second position.

The invention further relates to a domestic appliance, such as a vacuum cleaner, including a fragrance dispenser according to the invention.

The invention also relates to a fragrance dispensing cartridge carrying a fragrant substance and having vents for allowing air to pass for entraining fragrance from said cartridge and including retaining means for removably engaging a housing portion for mounting the cartridge in a position such that it is rotatably adjustable about an axis of rotation between at least a first position and a second position.

BRIEF SUMMARY OF THE INVENTION

A fragrance dispenser and a fragrance dispensing cartridge of the kinds mentioned in the opening paragraphs are known from practice in the form of the "Ambia Parfum System" with which some vacuum cleaners obtainable from Rowenta in Germany are equipped. In such vacuum cleaners, the fragrance dispensing cartridge includes a plate onto which a fragrant substance can be deposited. The cartridge is axially inserted into an essentially cylindrical recess in the housing of the vacuum cleaner and axially locked by twisting the cartridge so that rims and grooves at the proximal end of the cartridge and in the housing engage each other. By further twisting the cartridge, a vent in the cartridge is brought in-line with the air discharge passage in the housing portion allowing air to flow through the cartridge when the vacuum cleaner is in operation. The air flowing through the cartridge entrains fragrance substance. The rims and grooves at the proximal end of the cartridge allow axial displacement of the cartridge only when the cartridge is in a particular angular position relative to the housing.

A disadvantage of the known fragrance dispenser and of the known fragrance dispensing cartridge is that it is of relatively complex design. Furthermore, their operation is quite cumbersome. For instance, it can easily happen that the cartridge is axially released when the aim is to turn it into the position in which no (or least) scent is dispensed. The application of fragrant liquid to the cartridge entails strong scent emissions and spilling can easily occur and entails prolonged scent emissions from the spilled liquid.

From U.S. Pat. No. 4,554,698, a fragrance dispensing arrangement for a vacuum cleaner is known which includes a cartridge in the form of a drawer containing a tablet of scented material. The cartridge is mounted in a recess when the dispensing arrangement is in operative condition and can be shifted laterally in the recess to adjust the amount of air flowing through the drawer and entraining the scenting substance. This fragrance dispensing arrangement is also of a relatively complicated design. Furthermore, it occupies relatively much space, because the recess must be large enough to allow lateral shifting of the drawer. The front end of the drawer is relatively wide, because it includes flanges closing off the portions of the recess next to the drawer.

Similar disadvantages apply to a vacuum cleaner with a scent dispensing arrangement as known from U.S. Pat. No. 5,511,278. In this arrangement, the cartridge is formed by a slide member inserted in a recess. The slide member has a pocket for containing a scent tablet. The slide member and its pocket move sidewards to be centered on or offset from a slot in the hard bag of the vacuum cleaner through which discharge air flows.

It is an object of the present invention to provide a fragrance dispenser and a fragrance dispensing cartridge of the kinds mentioned in the opening paragraphs, for example, .a fragrance dispenser comprising a housing portion through which an air discharge passage interconnecting an upstream side of said housing portion and a downstream side of said housing portion extends, and a cartridge carrying a fragrant substance and having vents for allowing air to pass for entraining fragrance from said cartridge, wherein the cartridge is removably mounted and rotatably adjustable about an axis of rotation between at least a first position and a second position, at least a portion of at least one of said vents being obstructed by said housing portion if said cartridge is in said first position and being open if said cartridge is in said second position, or a domestic appliance, such as a vacuum cleaner, including such a fragrance dispenser according to the invention, or a fragrance dispensing cartridge carrying a fragrant substance and having vents for allowing air to pass for entraining fragrance from said cartridge and including retaining means for removably engaging a housing portion for mounting the cartridge in a position such that it is rotatably adjustable about an axis of rotation between at least a first position and a second position, in each case comprising a cartridge that is adjustable for varying the emission of fragrance, but wherein the cartridge is easier to mount.

To achieve this object, a fragrance dispenser according to the present invention is characterized in that said cartridge is removable in a direction transverse to said axis of rotation.

To achieve this object, a fragrance dispensing cartridge according to the invention is characterized in that the retaining means are adapted for engaging and releasing the housing portion in a direction transverse to said axis of rotation.

As a result of the invention, the means for retaining the cartridge in the mounted condition do not need to provide for selective axial retaining and rotational guidance of the cartridge in accordance with the angular position of the cartridge, so that simple means are sufficient for retaining the cartridge mounted to the housing portion and the mounting operation can be simplified.

It is a further object of the invention to provide a fragrance dispenser and a fragrance dispensing cartridge of the kinds mentioned in the opening paragraphs, wherein the handling of the fragrant substance in the cartridge is facilitated.

To achieve this further object, a fragrance dispenser and a fragrance dispensing cartridge according to the invention are characterized in that said cartridge contains a granular fragrance carrier substrate.

The invention also relates to a domestic appliance which includes a fragrance dispenser according to the invention. The invention is particularly suitable for use in vacuum cleaners.

Particular embodiments of the invention are set forth in the following description.

BRIEF DESCRIPTION OF THE SEVERAL VIEWS OF THE DRAWING(S)

Further features, effects and details of the invention will be apparent from the following detailed description in which reference is made to examples of fragrance dispensers according to the invention. In the figures.

DETAILED DESCRIPTION OF THE INVENTION

Figure 5:
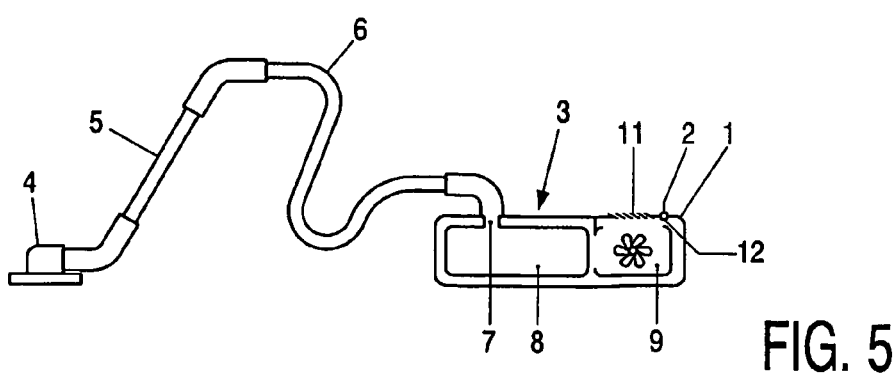
FIG. 5 is a schematic cross section of a vacuum cleaner including a fragrance dispenser according to the invention.

In FIGS. 1–4, a fragrance dispenser according to the invention is shown which includes a housing portion 1 and a fragrance-carrying cartridge 2 removably mounted to the housing portion 1. A possible location of the housing portion 1 and of the cartridge 2 according to the present example on a vacuum cleaner 3 is shown in FIG. 5. This vacuum cleaner 3 has a suction nozzle 4 connected to a tube 5. The tube 5 is connected to a hose 6. The hose 6 is connected to an inlet passage 7 in a housing of a sledge type vacuum cleaner, which passage 7 leads to the internals of a dust bag 8. An air discharge duct 9 extends from the dust bag 8 through a ventilator unit 10 and air discharge passages 11, 12 to the environment of the vacuum cleaner 3. One of these passages 12 is part of the fragrance dispenser portion of the vacuum cleaner 3 and interconnects an upstream side (in this example formed by the duct 9) of the housing portion 1 and a downstream side 13 (in this example formed by the environment of the vacuum cleaner 3) of the housing portion 1.

The cartridge 2 carries a fragrant substance. According to the present example, the fragrant substance is carried by a substrate in the form of granules 14. In this form, handling of the material is relatively easy and spilling does not entail undesired strong scent emissions. On the other hand, air can easily pass through the granulate in the cartridge and the granules have an exterior surface exposed to the air flowing through the cartridge, which is large relative to the volume of the material. Compared with the use of tablets, an advantage of the use of granular fragrant material in a cartridge is that the design of the material need not be specifically adapted to fit in a particular cartridge type. Accordingly, the same granular material can be used in cartridges of various designs and granular fragrant material from various sources can be used in the same cartridge.

The granules 14 are preferably made of a scent absorbing polymer material. A material having particularly advantageous properties for this application is or includes for instance polyether-block-amide material. A further advantage of such material is that it has anti-static properties so that accumulation of static electricity, which can easily occur in the area of the often relatively warm outlet end of a vacuum cleaner, is counteracted.

A further advantage of using a scent absorbing polymer material, and particularly polyether-block-amide as at least a constituent therein, is that fragrance emission therefrom is spread quite evenly over time when the material is exposed to an airflow while fragrance shows little or no tendency to sweat out while the material is packaged.

The cartridge 2 is provided with inlet vents 15 and outlet vents 16 for allowing air to pass for entraining scent from the cartridge 2.

Figure 1:
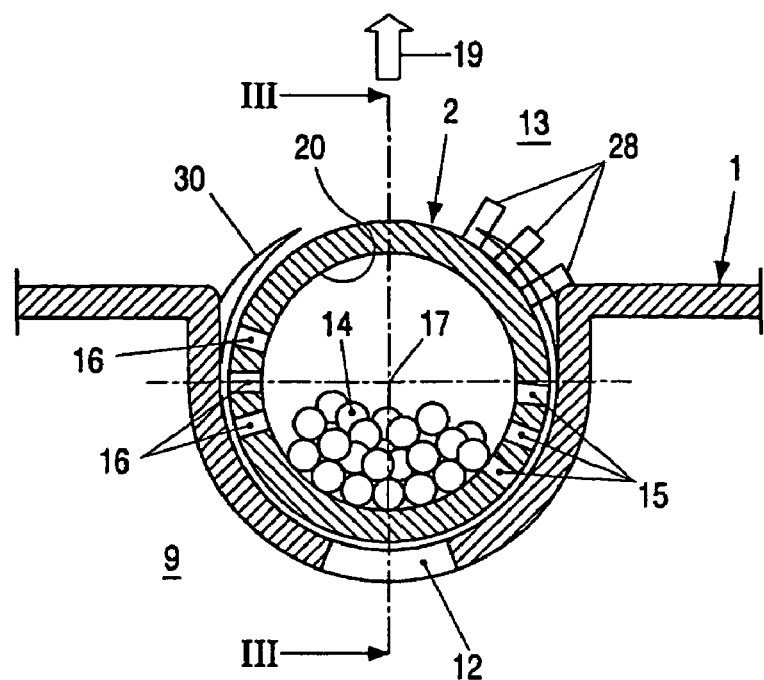
FIG. 1 is a cross section along the line I—I in FIG. 3 of an example of a fragrance dispenser according to the invention in a first operating condition.
Figure 2:
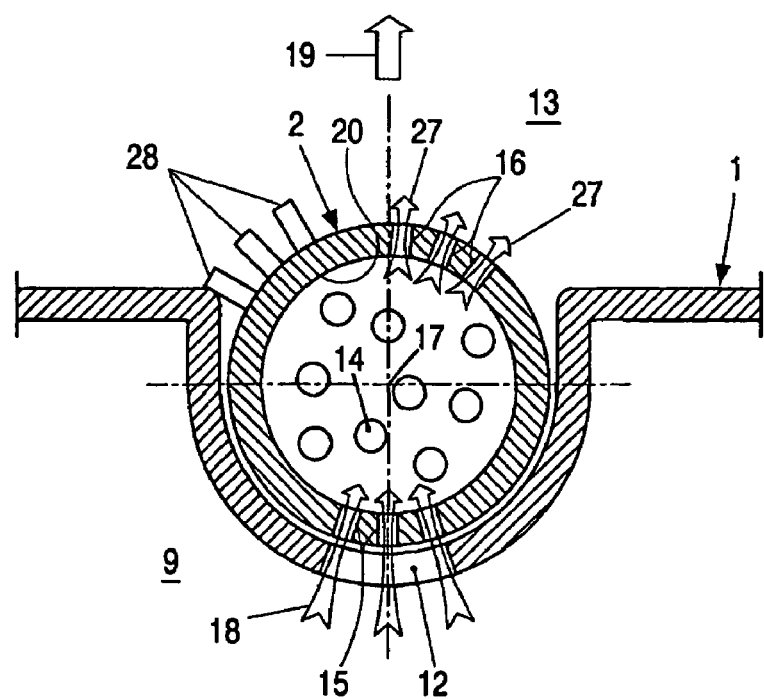
FIG. 2 is a cross section as shown in FIG. 1 of the same fragrance dispenser, but in a second operating condition.
Figure 3:
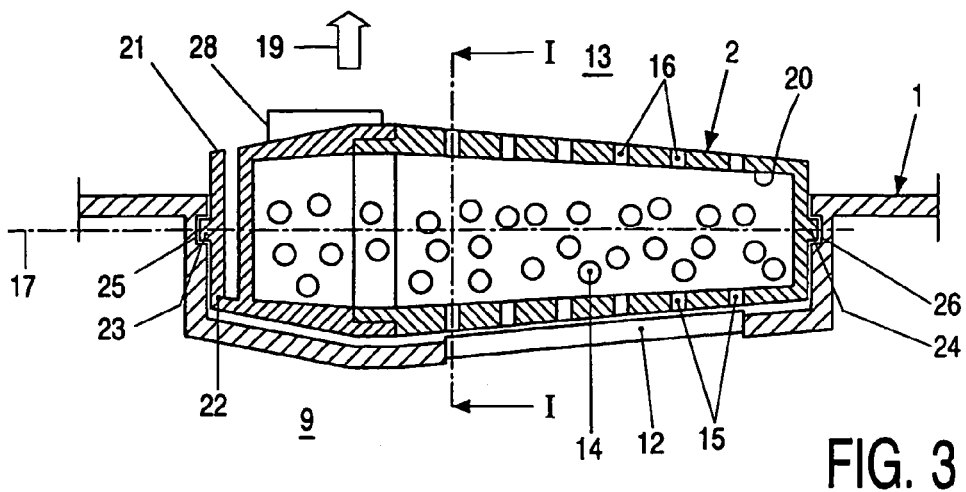
FIG. 3 is an axial cross section along the line III—III in FIG. 1.
Figure 4:
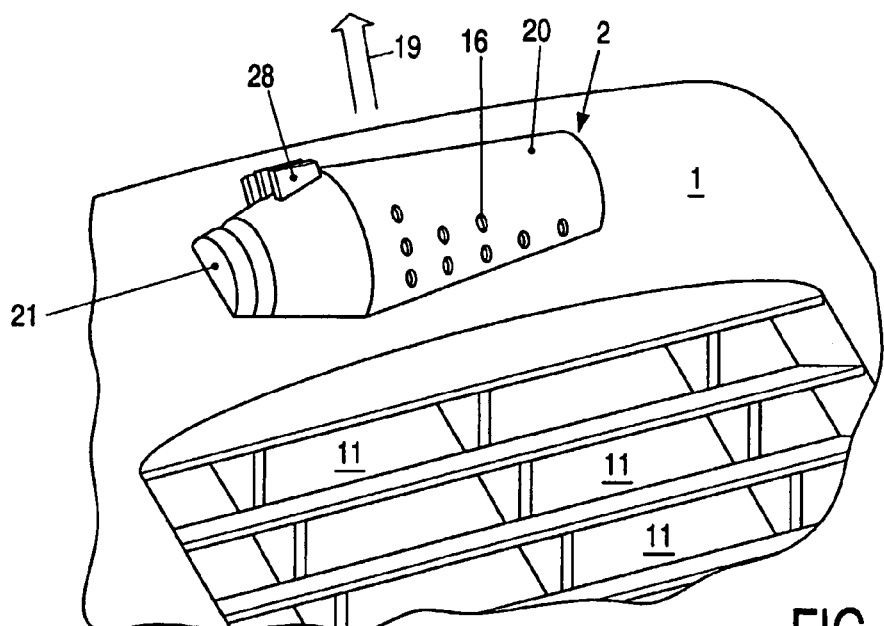
FIG. 4 is a perspective view of a portion of a domestic appliance according to the invention, in particular a vacuum cleaner, including a fragrance dispenser as shown in the preceding figures.

The cartridge 2 is removably mounted and rotatably adjustable about an axis of rotation 17 between at least a first position shown in FIG. 1 and a second position shown in FIG. 2. If the cartridge 2 is in the first position, the inlet vents 15 are obstructed by the housing portion 1. If the cartridge 2 is in the second position, the inlet vents 15 are in-line with the air discharge passage 12 in the housing portion 1 and therefore open so that air can pass through the inlet vents 15 as indicated by arrows 18.

An arrow 19 indicates the direction in which the cartridge 2 is removable from the housing portion 1. This direction is oriented transversely to the axis of rotation 17, so that a simple construction is sufficient for retaining the cartridge in the mounted condition.

The vents 15, 16 are arranged in a circumferential wall 20 of the cartridge 2. This allows the airflow through the vents 15, 16 to be adjusted across a wide range by rotational movement of the cartridge 2 through a relatively small angle, because the vents 15, 16 are located in the portion of the cartridge 2 where displacements are relatively large when the cartridge 2 is rotated. Furthermore, because the cartridge 2 is elongate in axial direction, the circumferential wall 20 has a relatively large surface to accommodate the vents 15, 16 and wall portions without perforations to be brought in line with the air discharge passage 12 when a flow of air through the cartridge 2 is to be prevented or at least reduced.

For retaining the cartridge 2 in the mounted position, the mounting structures engage the cartridge 2 from axially opposite sides, where the rotatable suspension of the cartridge 2 can easily be realized.

The cartridge 2 is resiliently, axially clamped. This allows the cartridge 2 to be held without play so that rattling is avoided. The clamping of the cartridge 2 further causes friction between the cartridge 2 and the housing portion 1 so that the cartridge 2 is held in the adjusted angular position. Furthermore, co-operating projections and recesses may be provided to hold the cartridge 2 in each of a plurality of angular positions relative to the housing portion 1.

The axial clamping of the cartridge 2 in the mounted condition is achieved by making sure that at least a portion of the cartridge 2 is axially compressible. This facilitates mounting and dismounting, because the user can compress the cartridge 2 with the same hand that holds the cartridge 2 during mounting and dismounting. According to the present example, the axial compressibility is achieved in a constructionally simple manner by providing the cartridge 2 with an arm 21 which extends from a fixed end 22 connected to the remainder of the cartridge 2 along an end face of the cartridge 2. The free end of the arm 21 can be pressed axially towards the remainder of the cartridge 2 against a spring force exerted by or via the arm 21.

The cartridge 2 is axially dividable for allowing access to the inside of the cartridge 2. Thus, the axial enclosure of the cartridge 2 in mounted condition also ensures that the cartridge 2 is maintained in the closed condition. In turn, this provides the advantage that constructional features for selectively opening the cartridge 2 and locking the cartridge in the closed condition can be dispensed with.

The rotatable suspension of the cartridge 2 is achieved in a simple manner by co-operating pins 23, 24 and recesses 25, 26 co-axial with the axis of rotation 17 and retaining the cartridge 2 in the mounted condition. Thus, the co-operating pins 23, 24 and recesses 25, 26 retain the cartridge 2 relative to the housing portion 1 and form the rotatable bearing of the cartridge 2 relative to the housing portion 1.

In the open condition, the vents 15, 16 are located in top and bottom portions of the cartridge 2, so that the air flows vertically through the cartridge 2. Because the inlet vents 15 are located in a bottom portion, preferably exclusively in a bottom half or quarter of the cartridge 2, it is ensured that the air is directed through the granular fragrant material 14 that accumulates in a bottom portion of the cartridge 2.

To obtain an effective distribution of the dispensed scent, it is further advantageous that the flow of the air leaving the cartridge 2 (arrows 27) is directed upward. To this end, the outlet vents 16 are arranged above the inlet vents 15 and preferably—at least partially—vertically above the inlet vents 15. At least when the inlet vents 15 are in-line with air discharge opening 12, so that the air flow through the vacuum cleaner is restrained relatively little (for instance while the nozzle 4 is not held against a surface), the upward air flow through the cartridge 2 may cause the granulate 14 to float up or to form a fluidized bed. Thereby, the granulate is mixed and the fragrance is evenly dispensed therefrom.

For easy adjustment of the angular position of the cartridge 2, the cartridge is further equipped with radially projecting operating handles 28. The radially projecting operating members 28 not only facilitate adjustment of the position of the cartridge 2, but also prevent that the cartridge is mounted in a wrong position and that the cartridge is rotated to a position outside the adjustment range. Furthermore, seen in axial cross-section, the cartridge 2 has an asymmetrical shape, which prevents mounting the cartridge 2 in a back-to-front orientation.

In the mounted condition, the cartridge 2 partially projects from the housing portion 1. This provides the advantage that the cartridge 2 occupies little space in the housing 7 of the vacuum cleaner 3. Furthermore, since the cartridge 2 is transparent, the interior of the cartridge 2 can easily be inspected visually for the presence of granules therein.

It will be clear to the skilled person, that many other embodiments are conceivable within the framework of the present invention. For instance, for retaining the cartridge 2 in position, instead of pins and recesses, flexible flanges or arms 30 can be provided as. Instead of in a vacuum cleaner, the fragrance dispenser can also be incorporated in other domestic appliances that displace air, for example air cleaners.

The invention claimed is:

1. A fragrance dispenser comprising:
   a housing portion through which an air discharge passage interconnecting an upstream side of said housing portion and a downstream side of said housing portion extends; and
   a cartridge carrying a fragrant substance and having vents for allowing air to pass for entraining fragrance from said cartridge;
   wherein the cartridge is removably mounted and rotatably adjustable about an axis of rotation between at least a first position and a second position, at least a portion of at least one of said vents being obstructed by said housing portion if said cartridge is in said first position and being open if said cartridge is in said second position;
   and wherein the cartridge is rotatably suspended relative to the housing portion by the action of cooperating mounting structures co-axial with the axis of rotation, said cartridge being removable in a direction transverse to said axis of rotation.

2. A fragrance dispenser as claimed in claim 1, characterized in that the cartridge has a circumferential wall extending around the axis of rotation, the vents being arranged in said circumferential wall.

3. A fragrance dispenser as claimed in claim 1, characterized in that mounting structures engage said cartridge from axially opposite sides.

4. A fragrance dispenser as claimed in claim 3, characterized in that said cartridge is resiliently, axially clamped.

5. A domestic appliance including a fragrance dispenser according to claim 4, said domestic appliance having a motor, a ventilator coupled to that motor and a housing including said housing portion, the ventilator communicating with said air discharge passage.

6. A fragrance dispenser as claimed in claim 1, characterized in that said cartridge is axially dividable for allowing access to the inside of said cartridge.

7. A fragrance dispenser as claimed in claim 1, characterized in that the fragrance dispenser further includes at least one co-operating pin and recess co-axial with said axis of rotation and retaining said cartridge in the mounted condition.

8. A domestic appliance including a fragrance dispenser according to claim 1, said domestic appliance having a motor, a ventilator coupled to that motor and a housing including said housing portion, the ventilator communicating with said air discharge passage.

9. A fragrance dispenser comprising:
   a housing portion through which an air discharge passage interconnecting an upstream side of said housing portion and a downstream side of said housing portion extends; and
   a cartridge carrying a fragrant substance and having vents for allowing air to pass for entraining fragrance from said cartridge;
   wherein the cartridge is removably mounted and rotatably adjustable about an axis of rotation between at least a first position and a second position, at least a portion of at least one of said vents being obstructed by said housing portion if said cartridge is in said first position and being open if said cartridge is in said second position;
   wherein said cartridge is axially dividable for allowing access to the inside of said cartridge, and is removable in a direction transverse to said axis of rotation.

10. A fragrance dispenser according to claim 9, characterized in that the vents include inlet vents and outlet vents, the inlet vents being located in a bottom portion of the cartridge.

11. A fragrance dispenser according to claim 10, characterized in that the inlet vents are located under the outlet vents for causing an upwardly directed flow through the cartridge when in operation.

12. A fragrance dispensing cartridge as claimed in claim 9, wherein a granular fragrance carrier substrate is present in said chamber.

13. A fragrance dispenser according to claim 12, characterized in that the granular fragrance carrier substrate comprises a scent absorbing polymer material.

14. A domestic appliance including a fragrance dispenser according to claim 9, said domestic appliance having a motor, a ventilator coupled to that motor and a housing including said housing portion, the ventilator communicating with said air discharge passage.

15. A fragrance dispenser comprising:
- a housing portion through which an air discharge passage interconnecting an upstream side of said housing portion and a downstream side of said housing portion extends; and
- a cartridge carrying a fragrant substance and having vents for allowing air to pass for entraining fragrance from said cartridge;
- wherein the cartridge is removably mounted and rotatably adjustable about an axis of rotation between at least a first position and a second position, at least a portion of at least one of said vents being obstructed by said housing portion if said cartridge is in said first position and being open if said cartridge is in said second position;
- wherein mounting structures engage said cartridge from axially opposite sides, said cartridge is resiliently, axially clamped, at least a portion of said cartridge is axially compressible, and said cartridge is removable in a direction transverse to said axis of rotation.

16. A domestic appliance including a fragrance dispenser according to claim 15, said domestic appliance having a motor, a ventilator coupled to that motor and a housing including said housing portion, the ventilator communicating with said air discharge passage.

* * * * *